United States Patent [19]

Coates, Jr. et al.

[11] 4,380,633

[45] Apr. 19, 1983

[54] METHINE DYES FROM TETRAHYDROQUINOLINE COMPOUNDS CONTAINING N-THIOETHER SUBSTITUENTS

[75] Inventors: Clarence A. Coates, Jr.; Max A. Weaver, both of Kingsport, Tenn.

[73] Assignee: Eastman Kodak Company, Rochester, N.Y.

[21] Appl. No.: 212,049

[22] Filed: Dec. 1, 1980

Related U.S. Application Data

[62] Division of Ser. No. 26,846, Apr. 4, 1979, Pat. No. 4,260,742, which is a division of Ser. No. 802,090, May 31, 1977, Pat. No. 4,161,601.

[51] Int. Cl.³ ................. C07D 401/12; C07D 413/12; C07D 417/12
[52] U.S. Cl. ..................................... 544/316; 542/427; 544/54; 544/55; 544/182; 544/333; 544/405; 546/152; 546/165; 546/172; 546/174; 546/175; 546/176; 546/177; 546/180; 546/157
[58] Field of Search ........................ 546/165; 542/427; 544/316, 405

[56] References Cited

U.S. PATENT DOCUMENTS

| | | | |
|---|---|---|---|
| 3,240,783 | 3/1966 | Straley et al. | 546/165 |
| 3,247,211 | 4/1966 | Weaver et al. | 546/165 |
| 3,631,049 | 12/1971 | Straley et al. | 546/165 |
| 3,917,604 | 11/1975 | Hoyle | 546/165 |
| 4,077,962 | 3/1978 | Beecken | 546/165 |
| 4,088,673 | 5/1978 | Gomm et al. | 546/165 |
| 4,172,944 | 10/1979 | Beecken | 546/165 |

*Primary Examiner*—Donald G. Daus
*Assistant Examiner*—James H. Turnipseed
*Attorney, Agent, or Firm*—Donald W. Spurrell; Daniel B. Reece, III

[57] ABSTRACT

Methine dyes from tetrahydroquinoline compounds containing N-thioether substituents, in general produce bright yellow shades when applied to polyester fabrics by conventional dyeing procedures, have improved properties such as dyeability, fastness to light, resistance to sublimation, insensitivity to pH changes, and dye at the boil and under pressure to the same depth of shade. These compounds are particularly useful in the thermal fixation technique for dyeing polyester materials.

9 Claims, No Drawings

METHINE DYES FROM TETRAHYDROQUINOLINE COMPOUNDS CONTAINING N-THIOETHER SUBSTITUENTS

This is a division of Application Ser. No. 26,846, filed Apr. 4, 1979, now U.S. Pat. No. 4,260,742, which is a division of Ser. No. 802,090, filed May 31, 1977, now U.S. Pat. No. 4,161,601.

The methine dyes of this invention derived from N-substituted tetrahydroquinoline compounds generally produce bright yellow shades on polyester fabrics and have one or more improved properties such as dyeability, fastness to light and crock, wash resistance to sublimation, good Barre coverage and leveling. The dyes generally are insensitive to pH changes, dye at the boil and under pressure to the same depth of shade, and are particularly useful in the thermal fixation technique for dyeing polyester materials.

The dyes of this invention have the following generic formula:

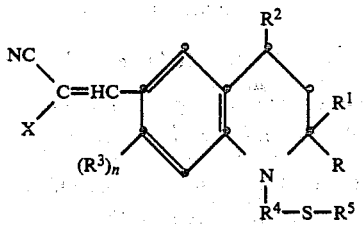

wherein X is selected from cyano, carbamoyl, lower alkyl carbamoyl, lower alkoxycarbonyl, lower alkylsulfonyl and arylsulfonyl; R, $R^1$, and $R^2$ are independently selected from hydrogen and lower alkyl; $R^3$ is selected from hydrogen, lower alkyl, lower alkoxy, fluorine, chlorine and bromine, and n is 0, 1 or 2; $R^4$ is lower alkylene; $R^5$ is selected from hydroxyethyl, acyloxyethyl and substituted and unsubstituted phenyl, benzyl, phenylethyl, cyclohexyl, pyridyl, quinolyl and pyrimidinyl radicals, and azolyl radicals having the formula

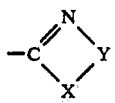

wherein Y is an ethylenically-unsaturated, two-atom chain of carbon atoms or a nitrogen and a carbon atom, X is an oxygen or sulfur atom or when Y is a two-atom carbon chain of atoms X can be a nitrogen atom, and when Y is a chain of two nuclear carbons of a phenylene ring, said azolyl radicals can be benzothiazolyl, benzoxazolyl or benzimidazolyl, each of which may be substituted with up to two groups independently selected from F, Cl, Br, $NO_2$, lower alkyl, lower alkylamino, lower alkanoylamino, lower alkoxy, hydroxy and cyano. The term "lower" as used herein is from 1–8 carbons.

The $R^5$ phenyl, benzyl and cyclohexyl radicals may be substituted with such groups as lower alkyl, lower alkoxy, lower alkoxycarbonyl, lower alkylether, hydroxy, cyano, fluorine, chlorine, bromine and nitro. Typical are p-chlorophenyl, m-bromophenyl, m-nitrophenyl, p-tolyl, p-anisyl, o,p-dichlorophenyl, p-butoxyphenyl, p-ethylphenyl, p-ethylbenzyl, p-methoxybenzyl, m-bromobenzyl, o,p-dichlorobenzyl, p-methoxycarbonylbenzyl, p-hydroxybenzyl, m-cyanobenzyl, 3-methylcyclohexyl, 4-methylcyclohexyl and 3,3,5-trimethylcyclohexyl. The pyridyl, quinolyl and pyrimidinyl radicals may be substituted with lower alkyl, such as 4-methyl-2-pyridyl, 7-ethyl-2-quinolyl and 4,6-dimethyl-2-pyrimidinyl.

The —X—Y— atoms of above $R^5$ may complete, for example, thiazolyl (—S—C=C—), isothiazolyl (—C=C—S—), oxazolyl, (—O—C=C—), isoxazolyl (—C=C—O—), imidazolyl (—N—C=C—), thiadiazolyl (—S—C=N— or —S—N=C—), and oxadiazolyl (—O—C=N— or —O—N=C—) radicals.

The carbons and any secondary nitrogen atoms of these radicals may be substituted, such as, 5-phenyl-1,3,4-oxazol-2-yl, 5-acetamido-1,3,4-thiadiazol-2-yl, 6-methyl-2-benzothiazolyl, 4,6-dichloro-2-benzothiazolyl, 6-cyano-2-benzoxazolyl, 6-methylsulfonyl-2-benzothiazolyl, 5-methoxy-2-benzoxazolyl, 6-nitro-2-benzothiazolyl, 2-benzimidazolyl, 6-thiocyano-2-benzothiazolyl, 2-thiazolyl, and 4,6-di-bromo-2-benzothiazolyl.

Preferred groups represented by $R^5$ have the formulae

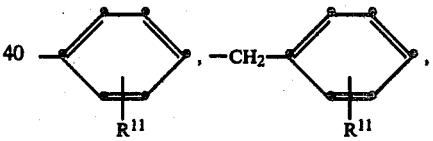

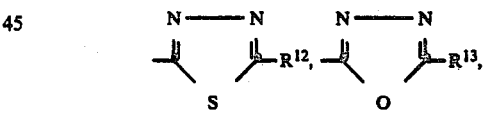

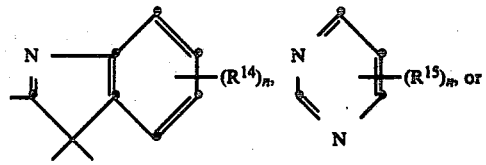

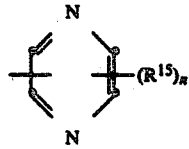

wherein $R^{11}$ is hydrogen, lower alkyl, lower alkoxy, F, Cl or Br;

$R^{12}$ is hydrogen, lower alkanoylamino or lower alkylsulfonamido;

$R^{13}$ is hydrogen, lower alkyl, phenyl or phenyl substituted with lower alkyl, lower alkoxy, F, Cl or Br;

$R^{14}$ is hydrogen, lower alkyl, lower alkoxy, F, Cl, Br, nitro, lower alkylsulfonyl, cyano or thiocyanato;

$R^{15}$ is hydrogen or lower alkyl;

X is —O—, —S— or —NH—; and n' is 1 or 2; and n is 0, 1 or 2.

The most preferred group of the above dyes are of the generic formula of page 2 wherein R, $R^1$, $R^2$ and $R^3$ are individually selected from hydrogen and methyl, X is cyano, $R^4$ is ethylene, and $R^5$ is 2-benzothiazolyl or 2-benzoxazolyl. Of these, the preferred dye is R, $R^1$ and $R^2$ as methyl, $R^3$ as hydrogen, X as cyano, and $R^5$ as 2-benzothiazolyl. This dye has particularly exceptional sublimation fastness, fastness to light, crock fastness, pH stability, build-up, leveling properties and good energy of application properties.

These compounds are particularly distinguished from the previously known tetrahydroquinoline methine dyes, such as those disclosed in U.S. Pat. No. 3,247,211 and U.S. Pat. No. 3,240,783 by improved pH stability. The previously known tetrahydroquinoline compounds have been limited in utility in the dyeing of polyester fabrics because of loss of color under high pH (6–8) conditions during the dyeing operation. The subject dyes are stable at high pH and result in full color yield and complete utilization of the dye even at pH levels of 8 or above.

The quinoline compounds used as starting materials for the present dyes are described in Elderfield's review (R. C. Elderfield, "Heterocyclic Compounds," Volume 4, John Wiley and Sons, Inc., New York, N.Y., 1952). Other references are J. Gagan and D. Lloyd, Chem. Communications, 1967, pp 1043–1044, Roberts and Turner, J. Chem. Soc., 1927, 1832, Houben-Weyl, Volume II, Part 3, p. 326, R. M. Acheson, "An Introduction to the Chemistry of Heterocyclic Compounds," Interscience Publishers, Inc., New York, N.Y., 1960, Chapter VI. The reduction of the quinoline compounds to the 1,2,3,4-tetrahydroquinoline derivatives is a well-known reaction.

PREPARATION OF N-HALOALKYLTETRAHYDROQUINOLINE INTERMEDIATES

EXAMPLE 1

350.0 Grams 2,2,4-trimethyl-1,2,3,4-tetrahydroquinoline, 2000 ml ethanol, and 110 grams ethylene oxide are heated in an autoclave for 12 hours at 180° C. The alcohol is removed by distillation and the hydroxylated product crystallizes and is collected by filtration, giving a product melting at 66°–68° C.

EXAMPLE 2

219 Grams 1-(2-hydroxyethyl)-2,2,4-trimethyl-1,2,3,4-tetrahydroquinoline are added to 250 grams phosphorus oxychloride at such a rate that the temperature is maintained at 30°–40° C. The reaction is heated for two hours at 95° C., the reaction drowned in ice water (5–6 liters), the chlorinated product crystallized and collected by filtration. The product melts at 48°–49° C.

Examples of other N-haloalkyltetrahydroquinolines that can be prepared as above or by reaction with epichlorohydrin followed by simple acylation, include

EXAMPLE 3

N-(2-chloroethyl)-1,2,3,4-tetrahydroquinoline.

EXAMPLE 4

N-(2-chloroethyl)-2,7-dimethyl-1,2,3,4-tetrahydroquinoline.

EXAMPLE 5

N-(2-chloropropyl)-2,2,4-trimethyl-1,2,3,4-tetrahydroquinoline.

EXAMPLE 6

N-(3-chloro-2-hydroxypropyl)-2,2,4-trimethyl-7-bromo-1,2,3,4-tetrahydroquinoline.

EXAMPLE 7

N-(2-chloroethyl)-2,2,4,7-tetramethyl-1,2,3,4-tetrahydroquinoline.

EXAMPLE 8

N-(2-acetoxy-3-chloropropyl)-2,2,4,7-tetramethyl-1,2,3,4-tetrahydroquinoline.

PREPARATION OF THE ALDEHYDE INTERMEDIATES

EXAMPLE 9

25.2 Grams 1-(2-chloroethyl)-2,2,4,7-tetramethyl-1,2,3,4-tetrahydroquinoline, 13.8 grams potassium carbonate, 16.7 grams 2-mercaptobenzothiazole, and 100 ml dimethylformamide are refluxed for two hours, the reaction drowned in water, and the product extracted with chloroform to give 38 grams of the following structure:

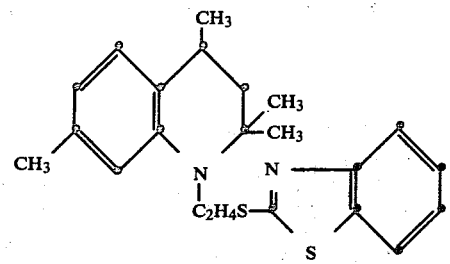

EXAMPLE 10

38.2 Grams 1-[2-[(2-benzothiazolyl)thio]ethyl]-1,2,3,4-tetrahydro-2,2,4,7-tetramethylquinoline are dissolved in 100 ml of dimethylformamide. To this is added 15.3 grams phosphorus oxychloride at 15°–20° C. After heating for one hour at 95° C., the reaction mixture is drowned in ice water, made basic with 50% sodium hydroxide and allowed to stand a few hours until the product solidifies. The aldehyde intermediate is collected by filtration, washed with water, and air dried. The product has the structure:

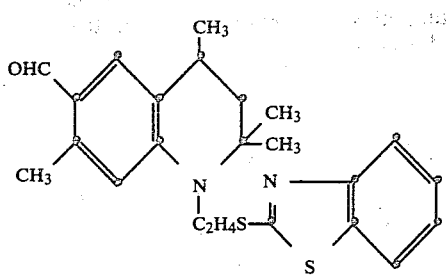

EXAMPLE 11

25.2 Grams 1-(2-chloroethyl)-2,2,4,7-tetramethyl-1,2,3,4-tetrahydroquinoline, 13.8 grams potassium carbonate, 11.1 grams benzenethiol and 150 ml dimethylformamide are refluxed for two hours, the reaction drowned in water, the product collected by filtration, washed with water, and dried in air. After recrystallization from methanol, the product has the following structure:

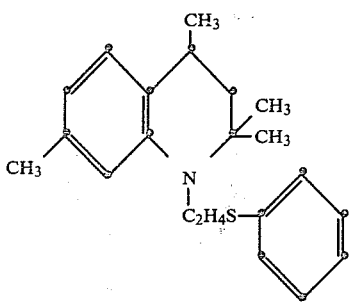

EXAMPLE 12

1.4 grams 1-(2-chloroethyl)-6-formyl-2,2,4,7-tetramethyl-1,2,3,4-tetrahydroquinoline, 0.8 gram 2-mercaptobenzoxazole, 0.8 gram potassium carbonate, and 20 ml dimethylformamide are heated at 140° C. with stirring for one hour. The reaction mixture is drowned in water, and the product collected by filtration to yield 1.95 grams of the following structure:

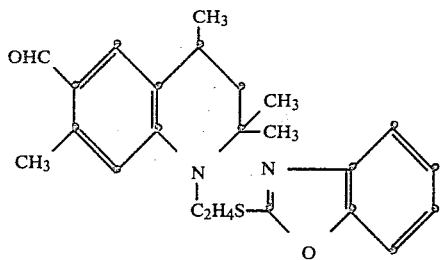

EXAMPLES OF DYE PREPARATION

EXAMPLE 13

4.1 Grams aldehyde from Example 10, 0.7 grams malononitrile, 0.2 ml piperidine, and 50 ml of methyl cellosolve are heated at 95° C. for one hour. The dye which separated upon cooling is collected by filtration, washed with methanol, and air-dried. The product which melts at 209°-11° C. dyes polyester fibers deep shades of yellow and has the formula:

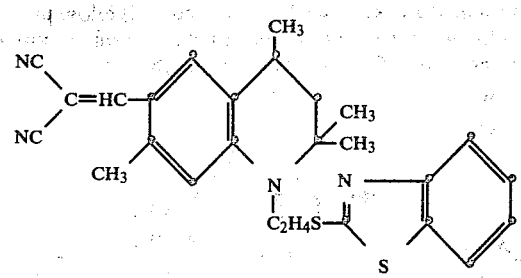

EXAMPLE 14

To a mixture of 125.0 grams 1-(2-hydroxyethyl)-2,2,4-trimethyl-1,2,3,4-tetrahydroquinoline in 125 ml of dimethylformamide is added, below 90° C., 125 ml of phosphorus oxychloride. The reaction mixture is heated two hours at 100° C., cooled, and neutralized to pH 5-6 with potassium carbonate. A quantity, 95.0 grams, 2-mercaptobenzothiazole is added and the mixture refluxed for one hour. After cooling to 45°-50° C., a slurry of 186 grams sodium acetate and 46.5 grams malononitrile in 800 ml isopropanol is added. The resulting mixture is refluxed for 2.0 hours. The reaction is cooled and water slowly added. The dye is collected by filtration, washed with water, and air dried. The product which melts at 165°-167° C. dyes polyester fibers bright yellow shades and has the following structure:

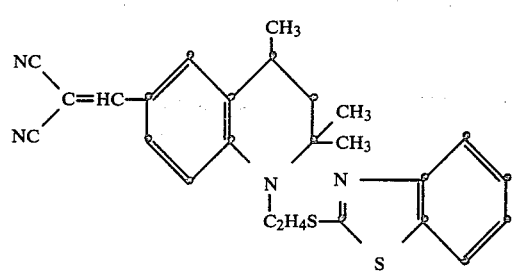

EXAMPLE 15

3.8 Grams of the aldehyde of Example 12, 1.0 gram methyl cyanoacetate, 25 ml alcohol, and 0.2 ml piperidine are refluxed together for one hour. The reaction mixture is allowed to cool and the product collected by filtration, washed with ethanol, and air dried. The product dyes polyester fibers deep shades of yellow and has the formula:

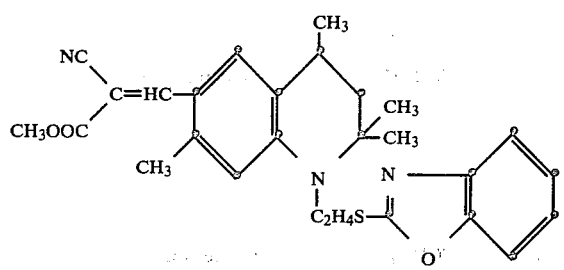

EXAMPLE 16

13.7 Grams 1-[2-[(2-benzothiazolyl)thio]ethyl]-6-formyl-1,2,3,4-tetrahydro-2,2,4-trimethylquinoline, 18.0 grams phenylsulfonylacetonitrile, 0.4 ml piperidine, and 100 ml ethanol are refluxed together for one hour. The reaction mixture is allowed to cool and the yellow product collected by filtration and air dried. The product colors polyester fiber yellow and has the formula:

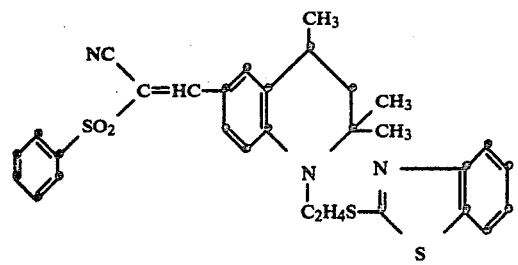

The dyes in the following table are prepared by the procedures illustrated above and have the following general formula:

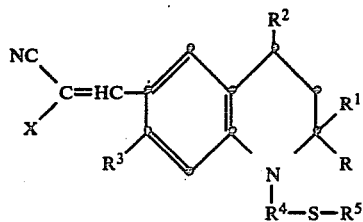

| Example No. | X | Substituents R, R¹, R², R³ | R⁴ | R⁵ |
|---|---|---|---|---|
| 17 | CN | NONE | —CH$_2$CH$_2$— | benzoxazol-2-yl |
| 18 | CN | 2,2,4-tri-CH$_3$ | —CH$_2$CH$_2$— | benzoxazol-2-yl |
| 19 | CN | 2,7-di-CH$_3$ | —CH$_2$CH$_2$ | benzoxazol-2-yl |
| 20 | CN | 2,2,4,7-tetra-CH$_3$ | —CH$_2$CH$_2$— | benzoxazol-2-yl |
| 21 | —SO$_2$C$_6$H$_5$ | 2,2,4,7-tetra-CH$_3$ | —CH$_2$CH$_2$— | benzoxazol-2-yl |
| 22 | —COOCH$_3$ | 2,2,4,7-tetra-CH$_3$ | —CH$_2$CH$_2$— | benzoxazol-2-yl |
| 23 | —CONH$_2$ | 2,2,4,7-tetra-CH$_3$ | —CH$_2$CH$_2$ | benzoxazol-2-yl |

-continued
| Example No. | X | Substituents R, R¹, R², R³ | R⁴ | R⁵ |
|---|---|---|---|---|
| 24 | —CONHC$_2$H$_5$ | 2,2,4,7-tetra-CH$_3$ | —CH$_2$CH$_2$— | 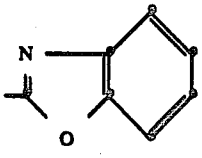 |
| 25 | —SO$_2$CH$_3$ | 2,2,4-tri-CH$_3$ | —CH$_2$CH$_2$CH$_2$— | 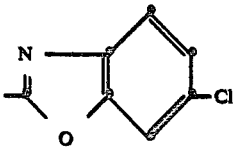 |
| 26 | CN | 2,2,4-tri-CH$_3$ | —CH$_2$CH$_2$— | 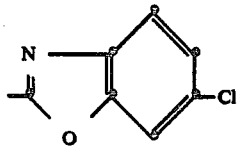 |
| 27 | CN | 2,7-di-CH$_3$ | —CH$_2$CH$_2$— | 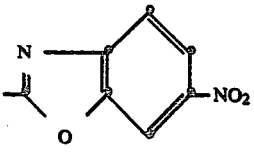 |
| 28 | CN | NONE | —CH$_2$CH$_2$— | 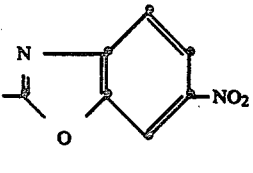 |
| 29 | CN | 7-Br—2,2,4-tri-CH$_3$ | —CH$_2$CH$_2$— | 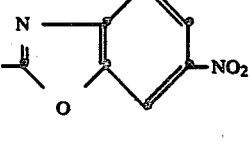 |
| 30 | CN | 2-CH$_3$—7-OCH$_3$ | —CH$_2$CH$_2$— | 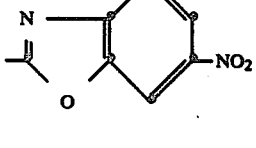 |
| 31 | CN | 7-CH$_3$ | —CH$_2$CH$_2$— | 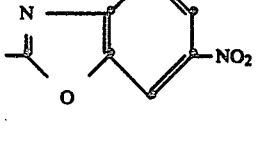 |
| 32 | —SO$_2$C$_6$H$_4$—p-Cl | 2,2,4,7-tetra-CH$_3$ | —CH$_2$CH$_2$— | 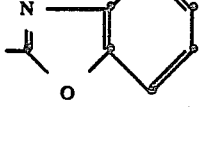 |

-continued

| Example No. | X | Substituents R, R¹, R², R³ | R⁴ | R⁵ |
|---|---|---|---|---|
| 33 | —COOC₂H₅ | 2,2,4,7-tetra-CH₃ | —CH₂CH₂— | benzoxazole |
| 34 | CN | 2,2,4-tri-CH₃ | —CH₂CH(CH₃)— | benzoxazole |
| 35 | CN | 2,2,4,7-tetra-CH₃ | —CH₂CH₂— | Br,CH₃-substituted benzoxazole |
| 36 | CN | 2,2,4,7-tetra-CH₃ | —CH₂CH₂— | —C₆H₁₁ |
| 37 | CN | 2,2,4,7-tetra-CH₃ | —CH₂CH₂— | —CH₂C₆H₅ |
| 38 | —CONH₂ | 2,2,4-tri-CH₃ | —CH₂CH(OH)CH₂— | —CH₂C₆H₅ |
| 39 | CN | 2,2,4-tri-CH₃ | —(CH₂)₄— | —CH₂C₆H₅ |
| 40 | CN | 2,2,4-tri-CH₃ | —CH₂CH(OCCCH₃)CH₂— | —CH₂C₆H₅ |
| 41 | CN | 2,2,4-tri-CH₃ | —CH₂CH(OCCCH₃)CH₂— | N-methylbenzimidazole |
| 42 | CN | 2,2,4-tri-CH₃ | —CH₂CH₂— | benzimidazole (NH) |
| 43 | —COOC₂H₅ | 2,2,4-tri-CH₃ | —CH₂CH₂— | N-ethylbenzimidazole |
| 44 | —SO₂CH₃ | 2,2,4-tri-CH₃ | —CH₂CH₂— | N-ethylbenzimidazole |

-continued

| Example No. | X | Substituents R, R¹, R², R³ | R⁴ | R⁵ |
|---|---|---|---|---|
| 45 | —CONHC₂H₅ | 2,2,4-tri-CH | —CH₂CH₂— | benzimidazol-2-yl (NH) |
| 46 | —CONHC₂H₅ | 2,2,4,7-tetra-CH₃ | —CH₂CH₂— | benzimidazol-2-yl (NH) |
| 47 | —CONHC₂H₅ | NONE | —CH₂CH₂— | benzimidazol-2-yl (NH) |
| 48 | CN | NONE | —CH₂CH₂— | benzimidazol-2-yl (NH) |
| 49 | CN | 2,7-di-CH₃ | —CH₂CH₂— | benzimidazol-2-yl (NH) |
| 50 | —SO₂C₆H₅ | 2,7-di-CH₃ | —CH₂CH₂— | benzimidazol-2-yl (NH) |
| 51 | —SO₂C₆H₅ | 7-CH₃ | —CH₂CH₂— | benzimidazol-2-yl (NH) |
| 52 | CN | 2-CH(CH₃)₂ | —CH₂CH₂— | benzimidazol-2-yl (NH) |

-continued

| Example No. | X | Substituents R, R¹, R², R³ | R⁴ | R⁵ |
|---|---|---|---|---|
| 53 | CN | 2,5,7-tri-CH₃ | —CH₂CH₂— | 2-(methylamino)phenyl benzimidazoline (NH) |
| 54 | CN | 7-OCH₃—2,2,4-tri-CH₃ | —CH₂CH₂— | benzimidazoline (NH) |
| 55 | —COOCH₃ | 2,2,4,7-tetra-CH₃ | —CH₂CH₂— | N-CH₃ benzimidazoline |
| 56 | CN | 2,2,4,7-tetra-CH₃ | —CH₂CH₂— | N-CH₃ benzimidazoline |
| 57 | CN | 2,2,4-tri-CH₃ | —CH₂CH₂— | N-CH₃ benzimidazoline |
| 58 | CN | 2,2,4-tri-CH₃ | —CH₂CH₂— | 5,6-dichloro benzimidazoline (NH) |
| 59 | —CONH₂ | 2,2,4-tri-CH₃ | —CH₂CH₂— | 5,6-dichloro benzimidazoline (NH) |
| 60 | —SO₂CH₃ | 2,2,4-tri-CH₃ | —CH₂CH₂— | 5,6-dichloro benzimidazoline (NH) |

-continued

| Example No. | X | Substituents R, R¹, R², R³ | R⁴ | R⁵ |
|---|---|---|---|---|
| 61 | CN | 2,2,4-tri-CH₃ | —CH₂CH₂— | benzothiazol-2-yl, 5-Cl |
| 62 | CN | 2,2,4,7-tetra-CH₃ | —CH₂CH₂— | benzothiazol-2-yl, 5-Cl |
| 63 | —COOC₂H₅ | 2,2,4,7-tetra-CH₃ | —CH₂CH₂— | benzothiazol-2-yl, 5-Cl |
| 64 | —COOC₂H₅ | 2,2,4,7-tetra-CH₃ | —CH₂CH₂— | benzothiazol-2-yl |
| 65 | —SO₂C₆H₄—p-CH₃ | 2,2,4,7-tetra-CH₃ | —CH₂CH₂— | benzothiazol-2-yl |
| 66 | —CONHC₂H₅ | 2,2,4,7-tetra-CH₃ | —CH₂CH₂— | benzothiazol-2-yl |
| 67 | —CONHC₂H₅ | 2,7-di-CH₃ | —CH₂CH₂ | benzothiazol-2-yl |
| 68 | CN | 2,7-di-CH₃ | —CH₂CH₂— | benzothiazol-2-yl |
| 69 | CN | NONE | —CH₂CH₂— | benzothiazol-2-yl |

-continued
| Example No. | X | Substituents R, R¹, R², R³ | R⁴ | R⁵ |
|---|---|---|---|---|
| 70 | CN | 7-Br—2,2,4-tri-CH₃ | —CH₂CH₂— | 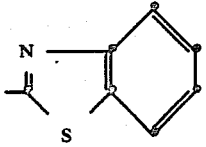 |
| 71 | CN | 2-CH₃—7-CH₃ | —CH₂CH₂— | 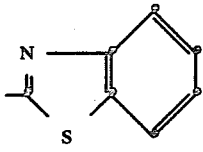 |
| 72 | CN | 2,2,4-tri-CH₃—5,8-di-OCH₃ | —CH₂CH₂— | 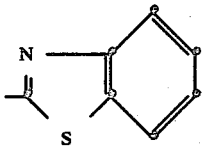 |
| 73 | —CN | 2,2,4,7-tetra-CH₃ | (CH₂)₄ | 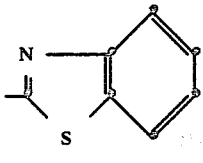 |
| 74 | —CN | 2,2,4,7-tetra-CH₃ | —CH₂CH(OH)CH₂ | 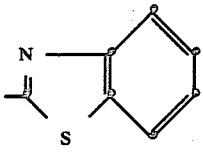 |
| 75 | —CN | 2,2,4,7-tetra-CH₃ | CH₂CH(OCOCH₃)CH₂ | 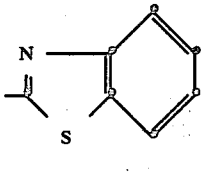 |
| 76 | —CN | 2-CH₃ | —CH₂CH₂— | 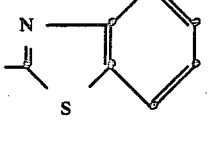 |
| 77 | —CN | 2-CH(CH₃)₂ | —CH₂CH₂— | 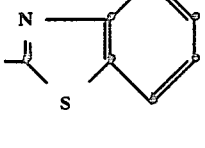 |
| 78 | —CO₂CH₃ | 2-CH(CH₃)₂ | —CH₂CH₂— | 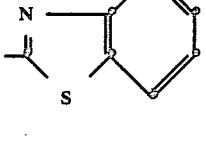 |

-continued

| Example No. | X | Substituents R, R¹, R², R³ | R⁴ | R⁵ |
|---|---|---|---|---|
| 79 | —CO₂CH₃ | 2,2,4-tri-CH₃ | —CH₂CH₂— | 6-chloro-7-chlorobenzothiazol-2-yl |
| 80 | CN | 2,2,4-tri-CH₃ | —CH₂CH₂— | 6-chloro-7-chlorobenzothiazol-2-yl |
| 81 | CONHC₄H₉—n | 2,2,4-tri-CH₃ | —CH₂CH₂— | 6-chloro-7-chlorobenzothiazol-2-yl |
| 82 | CN | 2,2,4-tri-CH₃ | —CH₂CH₂— | 6-methoxybenzothiazol-2-yl |
| 83 | CN | 2,2,4,7-tetra-CH₃ | —CH₂CH₂— | 6-methoxybenzothiazol-2-yl |
| 84 | CN | 2,2,4,7-tetra-CH₃ | —CH₂CH₂— | 4-chloro-6-methylbenzothiazol-2-yl |
| 85 | —SO₂C₆H₅ | 2,2,4,7-tetra-CH₃ | —CH₂CH₂— | 4-chloro-6-methylbenzothiazol-2-yl |
| 86 | —COOC₂H₅ | 2,2,4,7-tetra-CH₃ | —CH₂CH₂— | 4-chloro-6-methylbenzothiazol-2-yl |
| 87 | —COOC₂H₅ | 2,2,4,7-tetra-CH₃ | —CH₂CH₂— | C₆H₅ |
| 88 | —COOC₂H₅ | 2,2,4,7-tetra-CH₃ | CH₂CH₂CH₂ | C₆H₅ |
| 89 | CN | 2,2,4,7-tetra-CH₃ | CH₂CH₂CH₂ | C₆H₅ |
| 90 | CN | 2,2,4-tri-CH₃ | —CH₂CH₂— | C₆H₅ |

-continued

| Example No. | X | Substituents R, R¹, R², R³ | R⁴ | R⁵ |
|---|---|---|---|---|
| 91 | CN | 2,2,4-tri-CH₃ | —CH₂CH₂— | pyridyl |
| 92 | —SO₂CH₃ | 2,2,4-tri-CH₃ | —CH₂CH₂— | pyridyl |
| 93 | —CONH₂ | 2,2,4,-tri-CH₃ | —CH₂CH₂— | pyridyl |
| 94 | CN | 2,2,4,7-tetra-CH₃ | —CH₂CH₂— | pyridyl |
| 95 | CN | 2,2,4,7-tetra-CH₃ | —CH₂CH₂— | pyrazinyl |
| 96 | CN | 2,2,4,7-tetra-CH₃ | —(CH₂)₄ | pyrazinyl |
| 97 | —CONH₂ | 2,2,4,7-tetra-CH₃ | —(CH₂)₄ | pyrazinyl |
| 98 | —SO₂C₆H₅ | 2,2,4,7-tetra-CH₃ | —CH₂CH₂— | pyrazinyl |
| 99 | —COOC₂H₅ | 2,2,4,7-tetra-CH₃ | —CH₂CH₂— | pyrazinyl |

-continued

| Example No. | X | Substituents R, R¹, R², R³ | R⁴ | R⁵ |
|---|---|---|---|---|
| 100 | —COOC₃H₇—n | 2,2,4-tri-CH₃ | —CH₂CH₂— | pyrazine |
| 101 | —COOC₂H₅ | 2,2,4-tri-CH₃ | —CH₂CH₂— | 3,5-di-CH₃-pyrazine |
| 102 | CN | 2,2,4-tri-CH₃ | —CH₂CH₂— | 3,5-di-CH₃-pyrazine |
| 103 | CN | 2,2,4,7-tetra-CH₃ | —CH₂CH₂— | 3,5-di-CH₃-pyrazine |
| 104 | —COOCH₃ | 2,2,4,7-tetra-CH₃ | —CH₂CH₂— | 3,5-di-CH₃-pyrazine |
| 105 | —COOCH₃ | 2,2,4,7-tetra-CH₃ | —CH₂CH₂— | 2-NHCOCH₃-1,3,4-thiadiazole |
| 106 | CN | 2,2,4,7-tetra-CH₃ | —CH₂CH₂— | 2-NHCOCH₃-1,3,4-thiadiazole |
| 107 | CN | 2,2,4-tri-CH₃ | —CH₂CH₂— | 2-NHCOCH₃-1,3,4-thiadiazole |
| 108 | CN | 7-Br—2,2,4-tri-CH₃ | —CH₂CH₂— | 2-NHCOCH₃-1,3,4-thiadiazole |
| 109 | CN | 2-CH₃ | —CH₂CH₂— | 2-NHCOCH₃-1,3,4-thiadiazole |

-continued

| Example No. | X | Substituents R, R¹, R², R³ | R⁴ | R⁵ |
|---|---|---|---|---|
| 110 | CN | 2,2,4-tri-CH₃ | —CH₂CH₂— | benzoxazol-2-yl linked via N=N (2-position), fused benzene with O |
| 111 | —COOCH₃ | 2,2,4-tri-CH₃ | —CH₂CH₂— | benzoxazol-2-yl linked via N=N |
| 112 | CN | 2,2,4,7-tetra-CH₃ | —CH₂CH₂— | benzoxazol-2-yl linked via N=N |
| 113 | CN | 2,2,4,7-tetra-CH₃ | —CH₂CH₂— | 5-methyl-1H-1,2,4-triazol-3-yl linked via N=N |
| 114 | —SO₂C₆H₅ | 2,2,4,7-tetra-CH₃ | —CH₂CH₂— | 5-methyl-1H-1,2,4-triazol-3-yl linked via N=N |
| 115 | —SO₂C₆H₅ | 2,2,4,7-tetra-CH₃ | —CH₂CH₂— | —C₆H₄p-Cl |
| 116 | CN | 2,2,4,7-tetra-CH₃ | —CH₂CH₂— | —C₆H₄p-Cl |
| 117 | CN | 2,2,4-tri-CH₃ | —CH₂CH₂— | —C₆H₄p-Cl |
| 118 | CN | 2,2,4-tri-CH₃ | —CH₂CH₂ | quinolin-2-yl |
| 119 | CN | 2,2,4,7-tetra-CH₃ | —CH₂CH₂— | quinolin-2-yl |
| 120 | CN | 2,2,4,7-tetra-CH₃ | —(CH₂)₃— | quinolin-2-yl |
| 121 | —CONHC₄H₅ | 2,2,4,7-tetra-CH₃ | —(CH₂)₃— | quinolin-2-yl |
| 122 | CN | 2,2,4,7-tetra-CH₃ | —CH₂CH₂— | 1-methylimidazol-2-yl |

-continued

| Example No. | X | Substituents R, R¹, R², R³ | R⁴ | R⁵ |
|---|---|---|---|---|
| 123 | CN | 2,2,4-tri-CH₃ | —CH₂CH₂— | N-methylimidazole ring |
| 124 | —COOC₂H₅ | 2,2,4-tri-CH₃ | —CH₂CH₂— | N-methylimidazole ring |
| 125 | —CONH₂ | 2,2,4-tri-CH₃ | —CH₂CH₂— | N-methylimidazole ring |
| 126 | CN | 2,2,4-tri-CH₃ | —CH₂CH₂— | —C₆H₁₁ |
| 127 | —COOCH₃ | 2,2,4-tri-CH₃ | —CH₂CH₂— | —C₆H₁₀—3-CH₃ |
| 128 | CN | 2,2,4,7-tetra-CH₃ | —CH₂CH₂— | —C₆H₁₀—3-CH₃ |
| 129 | CN | 2,2,4,7-tetra-CH₃ | —CH₂CH₂— | benzothiazole-NHCOCH₃ |
| 130 | COOCH₃ | 2,2,4,7-tetra-CH₃ | —CH₂CH₂— | benzothiazole-NHCOCH₃ |
| 131 | COOCH₃ | 2,2,4-tri-CH₃ | —CH₂CH₂— | benzothiazole-NHCOCH₃ |
| 132 | CN | 2,2,4-tri-CH₃ | —CH₂CH₂— | triazine-diC₆H₅ |
| 133 | —COOC₂H₅ | 2,2,4-tri-CH₃ | —CH₂CH₂— | triazine-diC₆H₅ |
| 134 | —CN | 2,2,4,7-tetra-CH₃ | —CH₂CH₂— | triazine-diC₆H₅ |

-continued

| Example No. | X | Substituents R, R¹, R², R³ | R⁴ | R⁵ |
|---|---|---|---|---|
| 135 | —CONH₂ | 2,2,4,7-tetra-CH₃ | —CH₂CH₂— | 4-methylthiazol-2-yl |
| 136 | CN | 2,2,4,7-tetra-CH₃ | —CH₂CH₂— | 4-methylthiazol-2-yl |
| 137 | —SO₂C₆H₅ | 2,2,4,7-tetra-CH₃ | —CH₂CH₂— | 4-methylthiazol-2-yl |
| 138 | —SO₂C₆H₅ | 2,2,4,7-tetra-CH₃ | —CH₂CH₂— | 4,5-dimethylthiazol-2-yl |
| 139 | CN | 2,2,4,7-tetra-CH₃ | —CH₂CH₂— | 4,5-dimethylthiazol-2-yl |
| 140 | CN | 2,2,4-tri-CH₃ | —CH₂CH₂— | 4,5-dimethylthiazol-2-yl |
| 141 | COOCH₃ | 2,2,4-tri-CH₃ | —CH₂CH₂— | 4,5-dimethylthiazol-2-yl |
| 142 | COOCH₃ | 2,2,4-tri-CH₃ | —CH₂CH₂— | —CH₂C₆H₄—p-Cl |
| 143 | —SO₂CH₃ | 2,2,4-tri-CH₃ | —CH₂CH₂— | —CH₂C₆H₄—p-Cl |
| 144 | —SO₂CH₃ | 2,2,4-tri-CH₃ | —CH₂CH₂— | —C₆H₄—p-C(CH₃)₂ |
| 145 | CN | 2,2,4-tri-CH₃ | —CH₂CH₂— | —C₂H₄OC(O)CH₃ |
| 146 | CN | 2,2,4,7-tetra-CH₃ | —CH₂CH₂— | —C₂H₄OH |
| 147 | CN | 2,2,4,7-tetra-CH₃ | —CH₂CH₂CH₂— | —C₂H₄C₆H₅ |
| 148 | CN | 2,2,4,7-tetra-CH₃ | —CH₂CH₂CH₂— | 4,5,6,6-tetramethyl-5,6-dihydro-4H-1,3-thiazin-2-yl |
| 149 | CN | 2,2,4,7-tetra-CH₃ | —CH₂CH₂— | 4,5,6,6-tetramethyl-5,6-dihydro-4H-1,3-thiazin-2-yl |

-continued

| Example No. | X | Substituents R, R¹, R², R³ | R⁴ | R⁵ |
|---|---|---|---|---|
| 150 | CN | 2,2,4-tri-CH₃ | —CH₂CH₂— | 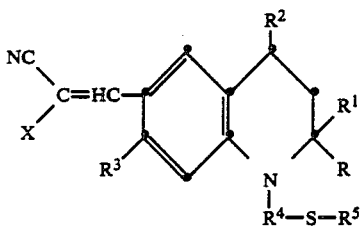 |
| 151 | CN | 2,2,4,7-tetra-CH₃ | —CH₂CH₂— | —C₆H₄—p-CH₃ |

The invention has been described in detail with particular reference to certain preferred embodiments thereof, but it will be understood that variations and modifications can be effected within the spirit and scope of the invention.

We claim:

1. A compound of the formula

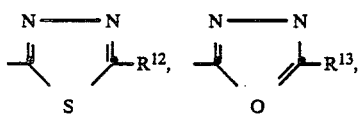

wherein X is selected from cyano, carbamoyl, lower alkylcarbamoyl, lower alkoxycarbonyl, lower alkylsulfonyl, and phenylsulfonyl; R, R¹, and R² are independently selected from hydrogen and lower alkyl; R³ is selected from hydrogen, lower alkyl, lower alkoxy, fluorine, chlorine, and bromine; R⁴ is lower alkylene; and R⁵ is selected from hydroxyethyl, acetoxyethyl, cyclohexyl, methylcyclohexyl, p-chlorophenylethyl, pyridyl, quinolyl, pyrimidinyl, thiadiazolyl, pyrazyl, and oxdiazolyl radicals.

2. A compound according to claim 1 wherein R⁵ has one of the formulae

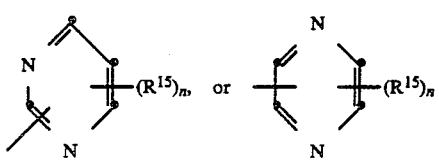

wherein
  R¹² is hydrogen, lower alkanoylamino or lower alkylsulfonamido;
  R¹³ is hydrogen, lower alkyl, phenyl or phenyl substituted with lower alkyl, lower alkoxy, F, Cl or Br;
  R¹⁵ is lower alkyl, or H when n is 0; and
  n is 0, 1 or 2.

3. A compound according to claim 1 having the formula

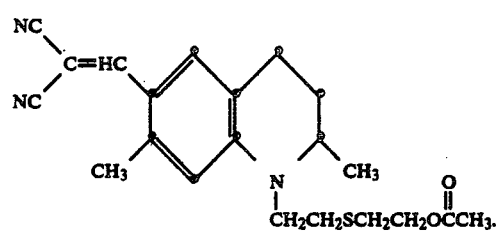

4. A compound according to claim 1 having the formula

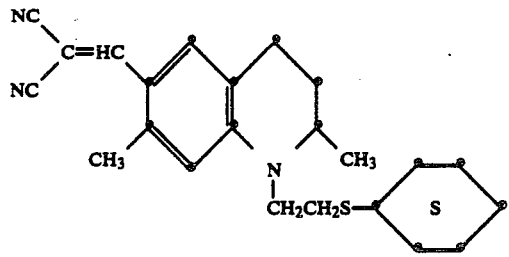

5. A compound according to claim 1 having the formula

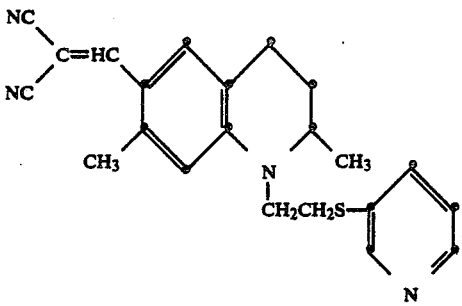

6. A compound according to claim 1 having the formula

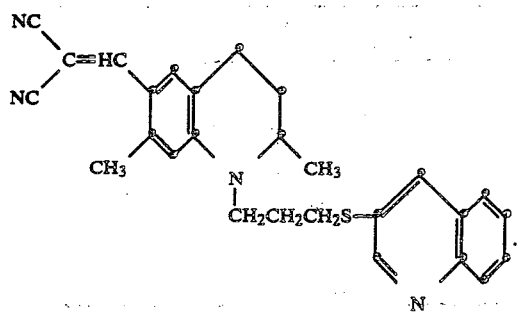
7. A compound according to claim 1 having the formula
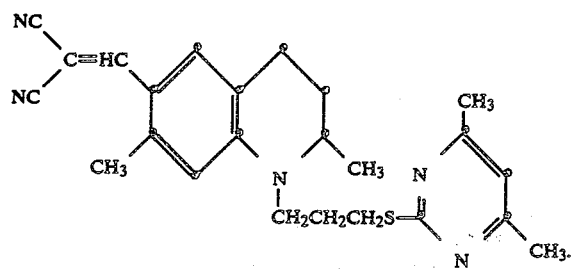
8. A compound according to claim 1 having the formula
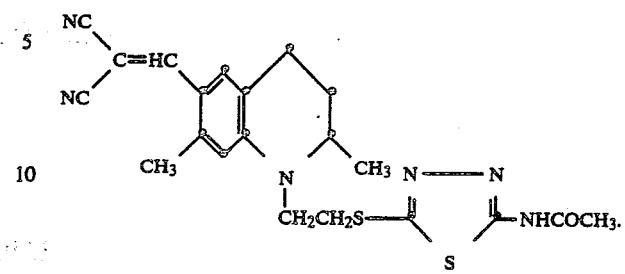
9. A compound according to claim 1 having the formula
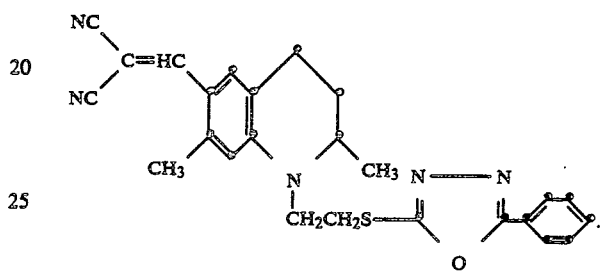
* * * * *